US011415693B2

(12) United States Patent
Long et al.

(10) Patent No.: US 11,415,693 B2
(45) Date of Patent: Aug. 16, 2022

(54) SPATIAL COHERENCE FEEDBACK FOR ADAPTIVE CLUTTER FILTERING

(71) Applicant: Duke University, Durham, NC (US)

(72) Inventors: Willie J. Long, Durham, NC (US); Gregg E. Trahey, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 17/080,527

(22) Filed: Oct. 26, 2020

(65) Prior Publication Data

US 2021/0124043 A1 Apr. 29, 2021

Related U.S. Application Data

(60) Provisional application No. 62/925,442, filed on Oct. 24, 2019.

(51) Int. Cl.
*G01S 15/89* (2006.01)
*A61B 8/08* (2006.01)

(52) U.S. Cl.
CPC ........ *G01S 15/8927* (2013.01); *A61B 8/5207* (2013.01); *A61B 8/5223* (2013.01); *G06T 2207/10132* (2013.01)

(58) Field of Classification Search
CPC .................. G06T 2207/10132; G01S 15/8981
See application file for complete search history.

(56) References Cited

U.S. PATENT DOCUMENTS

| 4,709,236 A * | 11/1987 | Taylor, Jr. | G01S 13/53 342/162 |
| 6,309,357 B1 * | 10/2001 | Guracar | G01S 7/52025 600/454 |
| 8,684,934 B2 * | 4/2014 | Kim | G01S 15/8981 600/453 |
| 2005/0049496 A1 * | 3/2005 | Guracar | G01S 7/52046 600/437 |

(Continued)

FOREIGN PATENT DOCUMENTS

| JP | 2012118040 A | * | 6/2012 |
| KR | 20070050694 A | * | 5/2007 |

OTHER PUBLICATIONS

KR-20070050694-A (Year: 2007).*

(Continued)

*Primary Examiner* — Oommen Jacob
*Assistant Examiner* — Nyrobi Celestine
(74) *Attorney, Agent, or Firm* — Kaplan Breyer Schwarz, LLP

(57) ABSTRACT

An ultrasound system that includes a transducer configured to acquire ensemble channel/echo data and a filter bank configured to receive the echo data from the transducer, wherein the echo data is passed through a plurality of clutter filters within the filter bank to realize a plurality of echo data outputs. A processor calculates a spatial coherence value from each of the plurality of echo data outputs, compares the spatial coherence values of each filter, and selects the filter that yields a best spatial coherence for subsequent velocity (Continued)

estimation used to generate an output image for clinical use, where the best spatial coherence value is a highest and best spatial coherence value among the set of spatial coherence values.

20 Claims, 15 Drawing Sheets

(56) References Cited

U.S. PATENT DOCUMENTS

| | | | | |
|---|---|---|---|---|
| 2005/0054931 | A1* | 3/2005 | Clark | A61B 8/06 600/453 |
| 2014/0316274 | A1* | 10/2014 | Koh | A61B 8/5269 600/453 |
| 2015/0272551 | A1* | 10/2015 | Jung | A61B 8/5207 600/443 |
| 2019/0380684 | A1* | 12/2019 | Insana | G06T 5/002 |

OTHER PUBLICATIONS

JP-2012118040-A (Year: 2012).*

Bjaerum et al., "Clutter Filters Adapted to Tissue Motion in Ultrasound Color Flow Imaging," IEEE Transactions on Ultrasonics, Ferroelectrics, and Frequency Control, vol. 49, No. 6, pp. 693-704, Jun. 2002 (Year: 2002).*

A. G. Tartakovsky, et al., "Adaptive Spatial-Temporal Filtering Methods for Clutter Removal and Target Tracking," IEEE Transactions—AES, pp. 1-14, Sep. 2007 (Year: 2007).*

J. Dahl, et al., "Harmonic Spatial Coherence Imaging: An Ultrasonic Imaging Method Based on Backscatter Coherence", IEEE Transactions on Ultrasonics, Ferroelectrics, and Frequency Control, vol. 59, No. 4, pp. 648-659, Apr. 2012 (Year: 2012).*

C. Kasai et al., "Real-Time Two-Dimensional Blood Flow Imaging Using an Autocorrelation Technique," in IEEE Transactions on Sonics and Ultrasonics, Dec. 1, 1985, doi: 10.1109/T-SU.1985.31615, pp. 458-464, vol. 32, No. 3.

Thanasis Loupas et al., "An axial velocity estimator for ultrasound flood flow imaging, based on a full evaluation of the Doppler equation by means of a two-dimensional autocorrelation approach," in IEEE Transactions on Ultrasonics, Ferroelectrics, and Frequency Control, Jul. 1, 1995, doi: 10.1109/58.393110, pp. 672-688, vol. 42, No. 4.

* cited by examiner

SPATIAL COHERENCE FEEDBACK FOR ADAPTIVE CLUTTER FILTERING

CROSS REFERENCE TO RELATED APPLICATIONS

This application claims the benefit of U.S. Provisional Application Ser. No. 62/925,442, filed Oct. 24, 2019, entitled "Spatial Coherence Feedback for Adaptive Clutter Filtering", which is incorporated herein by reference. If there are any contradictions or inconsistencies in language between this application and one or more of the cases that have been incorporated by reference that might affect the interpretation of the claims in this case, the claims in this case should be interpreted to be consistent with the language in this case.

STATEMENT REGARDING FEDERALLY SPONSORED RESEARCH

This invention was made with Government support under NIH Grant No. R01EB026574 awarded by the National Institutes of Health. The Government has certain rights in the invention.

FIELD OF THE INVENTION

The present invention relates to ultrasound systems in general. More particularly, the present invention relates to an ultrasound system configured to identify and extract, via clutter flittering, the most spatially coherent echo data to map to output images to be used for clinical purposes.

BACKGROUND OF THE INVENTION

Conventional ultrasound imaging includes a system and method for ultrasound clutter filtering. A processor iteratively selects an optimal high pass filter for progressive and ordered filtering of clutter from ultrasound color flow imaging data. The high pass filters also have different cutoff frequencies whereby each high pass filter is implemented using different structures.

Another conventional method for ultrasound clutter filtering employs adaptive filtering of clutter from a sample stream with a blood signal component and a clutter signal component. The adaptive filtering method estimates a signal strength of the sample stream and determines an order of a filter based on a relationship between a signal strength estimate and a signal strength threshold. An output stream has a reduced level of clutter in comparison to the blood signal component.

Still another previous method uses more than one clutter filter, where each clutter filter's magnitude versus frequency is optimized differently. Estimates of flow or movement are calculated from the data output of each clutter filter. The best attributes of each clutter filter are then used for imaging during clinical use.

Another conventional method uses an ultrasound system including an ultrasound data acquisition unit configured to transmit ultrasound signals to a target object and receive ultrasound echoes reflected from the target object, thereby acquiring ultrasound data. A processing unit is also configured to form a Doppler signal that corresponds to each of a plurality of pixels constructing a Doppler mode image based on the ultrasound data. The processing unit also adjusts coefficients of a clutter filter based on characteristics of the Doppler signal for each pixel performing clutter filtering on the Doppler signal.

Yet another previous method employs a fuzzy logic processor to determine when an adaptive wall filter can be turned off in response to the condition where a flow signal will be treated as a wall signal. The fuzzy logic processor determines whether a measured echo signal component that is to be filtered represents the wall velocity only. The fuzzy logic process determines that a LOW wall velocity with a wall variance at LOW and a wall power at HIGH, then the adaptive filter is turned on where LOW and HIGH are fuzzy values.

Including the previous methods described above, color flow imaging (CFI) is a standard mode on most, if not all, clinical ultrasound systems that are used commonly for diagnosing cardiovascular disease, performing biopsies, and providing clinical images, etc. Nevertheless, CFI is known for poor accuracy and sensitivity with regard to the presence of tissue and also transducer motion. The cause of the poor accuracy and sensitivity is often due to sub-optimal clutter filtering. In particular, clutter filters with low cutoff frequencies are susceptible to velocity underestimation by moving clutter. Clutter filters with high cutoff frequencies compromise flow detection.

Accordingly, methods have been developed to mitigate the problems due to sub-optimal clutter filtering, such as those described above. Moreover, additional methods include applying measurements of tissue motion prior to clutter filtering to downmix clutter signals or adjust the filter stopband. Other methods include using Eigen-filtering to remove slow-time signal components based on assumed thresholds for clutter velocity and magnitude.

Nevertheless, the problem of minimizing poor accuracy and sensitivity due to sub-optimal clutter filtering remains an issue among current ultrasound systems. Such systems include applying low fixed cutoff filtering and high fixed cutoff filtering systems.

A need exists for a fundamentally distinct approach to the methods described above. In other words, a distinct approach to adaptive clutter filtering is needed. Such an approach includes a method or design to inform clutter filter design using unique information that is not captured by either the magnitude or motion of pulse-echo data is provided. Such a method provides the added dimension needed to better discriminate between flow and clutter signals and also improve adaptive filtering under conditions where motion and magnitude-based methods fail.

SUMMARY OF THE INVENTION

The present invention enables an ultrasound system to identify a parameter (spatial coherence) to be used to apply to images for clinical use without some of the costs and disadvantages of the prior art. Embodiments of the present invention employ a real-time process that is applied continuously to filter an echo data signal, calculate spatial coherence values, and identify a filter that gives a best spatial coherence value, and then apply that filter to form an output image to be used for clinical use.

Like methods known in the prior art, the present invention utilizes color flow imaging (CFI), which is common in ultrasound imaging to determine fluid flow and blood in a subject/patient. However, CFI is known to have poor accuracy and sensitivity, especially in the presence of tissue and transducer motion. Sub-optimal clutter filtering leads to poor accuracy and sensitivity. Clutter filters with low cutoff frequencies, or low-fixed-frequency-cutoff filtering systems are susceptible to velocity underestimation. Further, high-fixed-frequency-cutoff filtering systems compromise slow flow detection by either removing low velocity signals or biasing velocity estimation by skewing the slow-time spectrum of echo data.

In marked contrast to the prior art, embodiments of the present invention enable more effective clutter filtering in ultrasound estimation. More specifically, the present invention passes ensemble channel data/pulse echo data through a bank of different clutter filters and the spatial coherence of the output of each filter is measured. A map of the spatial coherence values from each filter of the filter bank is generated and used to determine which of the filter outputs has the best spatial coherence. The filter whose output has the best spatial coherence is then designated as the "preferred filter" and is used for subsequent velocity estimations used to generate an output image during clinical use.

An illustrative embodiment of the present invention is an ultrasound system comprising a transducer configured to acquire ensemble channel/echo data. The ultrasound system also includes a filter bank configured to receive the echo data from the transducer, wherein the echo data is passed through one or more filters within the filter bank. The ultrasound system also includes a processor configured to calculate a spatial coherence value from echo data output of each filter of the filter bank. The processor compares the spatial coherence values of each filter and selects the filter which yields the output having the highest and best spatial coherence among all the filter outputs for subsequent velocity estimation. The selected filter is designated as the "preferred filter."

In some embodiments, the best spatial coherence is mapped to an output image.

In some embodiments, the echo data output from each filter of the filter bank is used to generate a map of the spatial coherence values.

In some embodiments, the echo data is passed through an Eigen-filter and an IIR filter in real-time based on a predicted target-motion-estimation accuracy. In some embodiments, this substantially optimizes the target-motion estimation.

In some embodiments, the echo data is passed through a bank of different clutter filters within the filter bank.

An embodiment of the present invention is an ultrasound system comprising: a transducer configured to acquire and transmit echo data; a filter bank with a plurality of clutter filters configured to receive the echo data from the transducer, wherein the echo data is passed through the plurality of clutter filters; and a processor configured to identify spatial coherence values from output echo data for each clutter filter, compare the spatial coherence values from the output echo data for each clutter filter, and identify the highest and best spatial coherence value and determine the preferred clutter filter for subsequent velocity estimations.

In some embodiments, the processor generates a map of the spatial coherence values from the output ensemble echo data to identify the best spatial coherence value.

In some embodiments, the echo data is passed through an FIR filter and an FFT filter in post-acquisition based on a target motion estimation accuracy. In some embodiments, this substantially optimizes the target-motion estimation.

In some embodiments, the clutter filter that yields the best spatial coherence is selected for subsequent velocity estimation.

Another embodiment of the present invention is a method comprising selecting a best spatial coherence by operations including: acquiring, by a transducer, ensemble channel/echo data; receiving, by a filter bank, the echo data from the transducer, wherein the echo data is passed through one or more filters within the filter bank; and calculating, by a processor, a spatial coherence value from echo data output of each filter of the filter bank, wherein the processor compares the spatial coherence values of each filter and identifies the filter that yields the best spatial coherence for subsequent velocity estimation.

In some of the embodiments, the processor uses the calculated spatial coherence values to identify the best spatial coherence.

In some of the embodiments, the processor outputs the best spatial coherence to the output image in real-time based on a target motion estimation accuracy.

In some of the embodiments, the processor uses the echo data output from each filter to generate the spatial coherence values and velocity estimates in post-acquisition time based on a target motion estimation accuracy. In some embodiments, this substantially optimizes the target-motion estimation.

In some of the embodiments, the processor generates the spatial coherence values to identify the filter to apply based on a target motion estimation accuracy. In some embodiments, this substantially optimizes the target-motion estimation.

Spatial coherence is measured at each pixel to assess local target motion accuracy at the output of each filter in the filter bank. The filter with the best spatial coherence then is used to estimate motion at that pixel, and thus optimize target-motion estimation accuracy.

DETAILED DESCRIPTION

Figure 1:
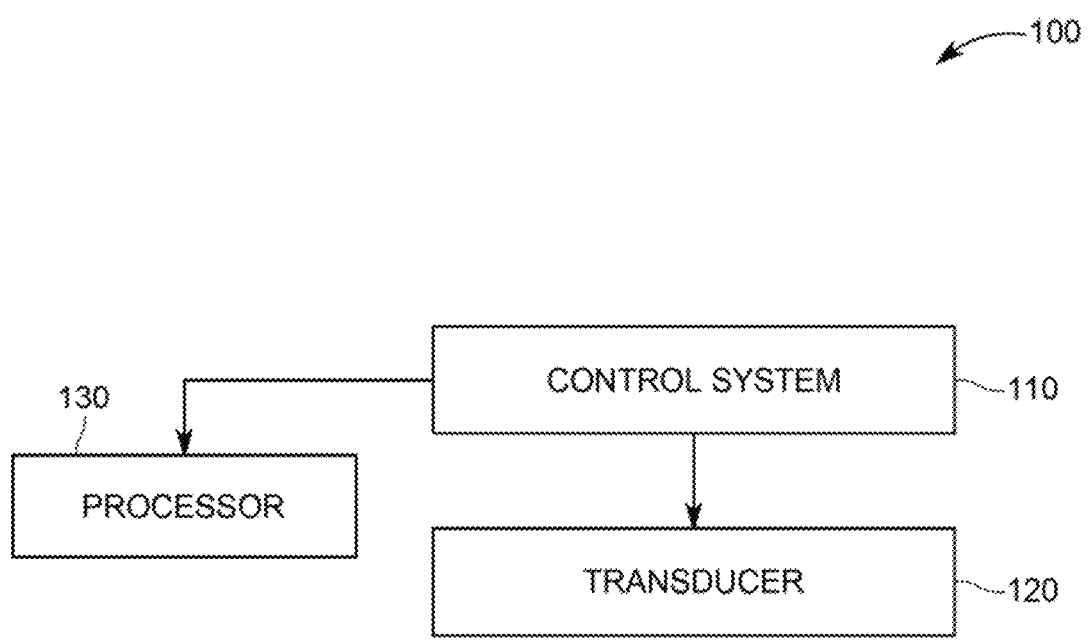
FIG. 1 depicts a block diagram of an ultrasound system in accordance with an illustrative embodiment of the present invention.

FIG. 1 depicts a block diagram of an ultrasound system 100. The ultrasound system 100 includes a control system 110 and a transducer 120, and a processor 130. The control system 110 includes input/output devices, a display, memory, an IIR filter bank, and a power source. Moreover, the control system 110 includes all of the elements that are typically found in a standard ultrasound system and that are necessary to perform ultrasound imaging.

The transducer 120 is a conventional ultrasound transducer that is configured to acquire ensemble channel data/echo data. The transducer 120 can transmit a series of pulses to interrogate motion in the imaging medium. The transducer 120 can also send echoes from a series of transmit pulses and received by individual elements, or echoes from neighboring groups of elements which have been delayed and summed, to the IIR filter bank. The IIR filter bank, with a plurality of clutter filters, filters the signal of the echo data through a plurality of filters configured within the IIR filter bank. The clutter filters, also known as wall filters, can be applied to the echoes from a series of pulses that are received either at individual array elements or the delayed and summed echoes from adjacent groups of elements.

The processor 130 measures the spatial coherence values from each filter of the IIR filter bank. The processor 130 calculates the spatial coherence between the filtered echoes from the individual array elements or groups of elements. The processor 130 also generates a map based on the spatial coherence value of each filter, and a map of the velocity estimates as well. Based on the map of the spatial coherence values, the processor also identifies the filter that yields the best spatial coherence. For the purposes of this Specification, including the appended claims, the "best spatial coherence" is defined as a maximum, optimum or target spatial coherence that has the highest spatial coherence value among the set of spatial coherence values determined for the output signals from the filters of the filter bank. The processor 130 can also identify the filter with the highest spatial coherence value as a preferred filter that is to be used to generate an output image for clinical use. The processor 130 can also map or apply the best spatial coherence to the output image to be used for clinical purposes (shown in more detail below and with reference to FIG. 2).

The above described process in FIG. 1, and similarly in FIGS. 2 and 7 described below can be applied at each image pixel. The best clutter filter is calculated and applied at each pixel. Further, a map of the best spatial coherence or the best clutter filter need not be made in order to use the preferred filter to generate an output image for clinical use and apply the best spatial coherence to the output image for clinical purposes. In some embodiments, the best clutter filter can be a weighted combination of some of the clutter filters in the filter bank. The best clutter filter can also be an arbitrarily shaped filter that is based on the spatial coherence measurements at each pixel.

The above-described process in FIG. 1, and also described below in FIGS. 2 and 7 can also be used for color flow imaging, Spectral Doppler imaging, and to Continuous Wave Doppler measurements.

Figure 2:
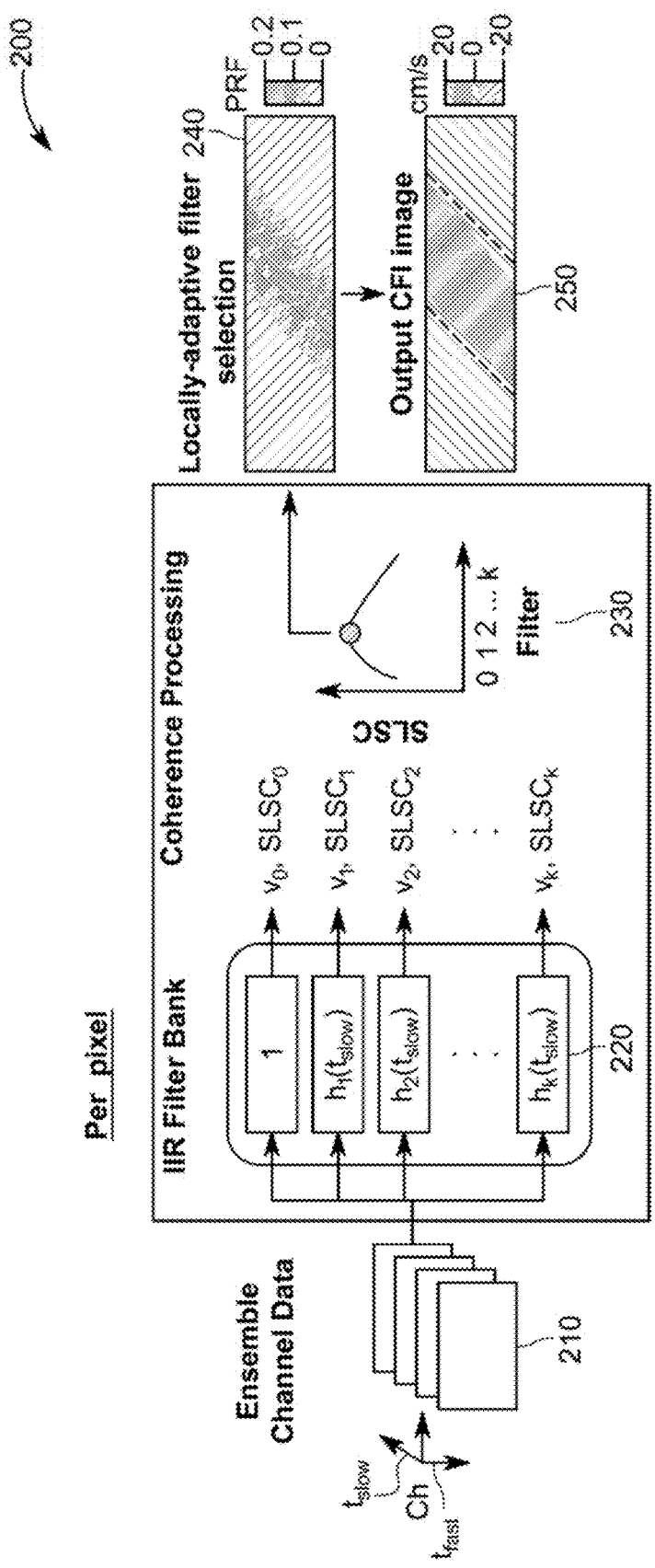
FIG. 2 depicts a processing pipeline of an ultrasound system in accordance with an illustrative embodiment of the present invention.

FIG. 2 illustrates a representative processing pipeline 200 for coherence-adaptive filtering that occurs in the ultrasound system 100. The pipeline 200 includes the elements described above for FIG. 1, including the transducer 120, the control system 110, and the processor 130. The transducer 120 acquires ensemble channel data/echo data 210. The transducer 120 transmits the echo data 210 to filter bank 220. In the depicted example, filter bank 220 includes a plurality of IIR filters; however, in some embodiments, filter bank 220 includes a different filter, such as FIR, Eigen-filters, FFT filters, and the like. The Filter bank 220 bandpass-filters the signal of the echo data 210. Within pipeline 200, processor 130 identifies the output echo data from each filter of filter bank 220. In addition, processor 130 generates a map 230 of spatial coherence values and also velocity estimates. Map 230 is used to compare the spatial coherence measurements between each filter and identify the best spatial coherence among the set of output signals. The processor 130 also compares the velocity estimates from each filter.

The spatial coherence provides unique information that not captured by either magnitude or motion, including the similarity between various backscattered echo signals. In addition, the spatial coherence provides an added dimension to make it easier to discriminate between flow signal and clutter signal. The spatial coherence improves adaptive filtering in situations where motion and magnitude-based methods are applied (such as when blood echoes and tissue echoes are similar in magnitude). The spatial coherence also enables accurate velocity estimation that would not ordinarily be enabled with magnitude and motion.

The spatial coherence is expressed in terms of a spatial separation of two points. The normalized spatial coherence is calculated for an array of elements. In the depicted example, the spatial coherence is calculated via a spatial domain approach; however, a frequency domain approach can be used without departing from the scope of the present disclosure.

Under the spatial domain approach, a normalized cross-correlation between all channel pairs is calculated over a chosen axial kernel to construct a full coherence curve.

In the frequency domain approach, a short-time Fourier transform is performed on signals in the channel domain, wherein a sliding window is used in the time dimension to calculate the complex frequency-domain representation of the signal. Further, a complex normalized dot product is taken between channel pairs and averaged.

In addition to the spatial domain approach and frequency domain approach, processor 130 can also calculate the spatial coherence utilizing a Sum-Absolute Difference (SAD) approaches, a Normalized SAD approach, and a Phase Difference approach using Loupas, Kasai or other algorithms and non-normalized correlations.

Processor 130 then determines a spatial coherence value that is intrinsic to target.

Processor 130 thereby generates a map 230 of the calculated spatial coherence values from each filter of the filter bank 220. The map 230 enables the processor 130 to compare the spatial coherence values to determine which spatial coherence value is the optimum spatial coherence value.

Processor 130 also identifies which filter of the filter bank 220 yields the best spatial coherence. As defined above for FIG. 1, the best spatial coherence refers to a maximum, optimum, or target spatial coherence that has the highest spatial coherence value among the set of spatial coherence values. Accordingly, as processor 130 identifies the best spatial coherence value and its associated filter, processor 130 also thereby performs locally adaptive filter selection 240. Processor 130 then designates the filter which yields the best spatial coherence as the "preferred filter" to be used for subsequent velocity estimation and generation of an output image 250 for clinical use.

Figure 3A:
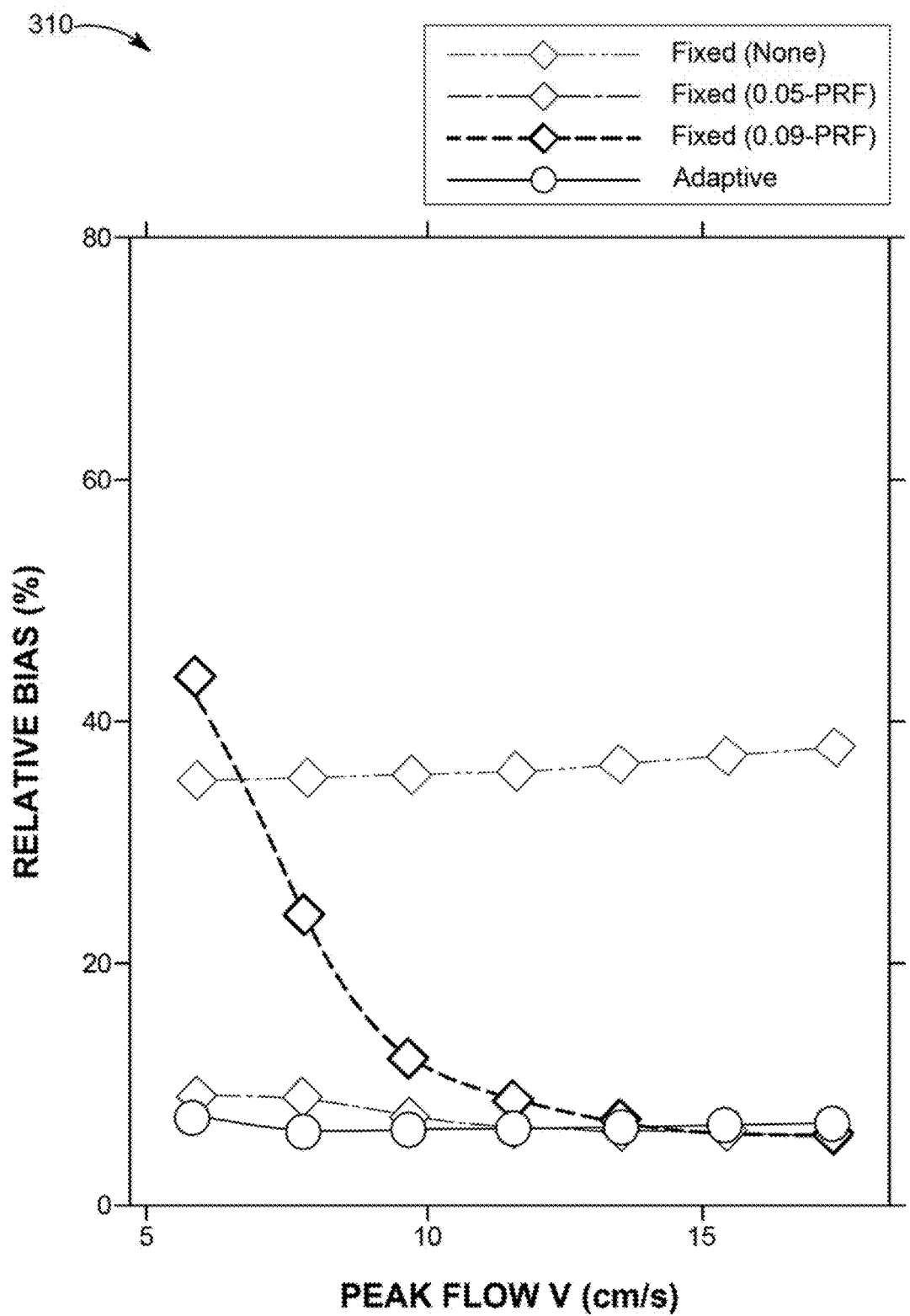
FIG. 3(A) depicts a graph illustrating a comparison of the peak flow velocity of a coherence-adaptive filter versus a non-filter, a 0.05-PRF Filter, and a 0.09-PRF filter.
Figure 3B:
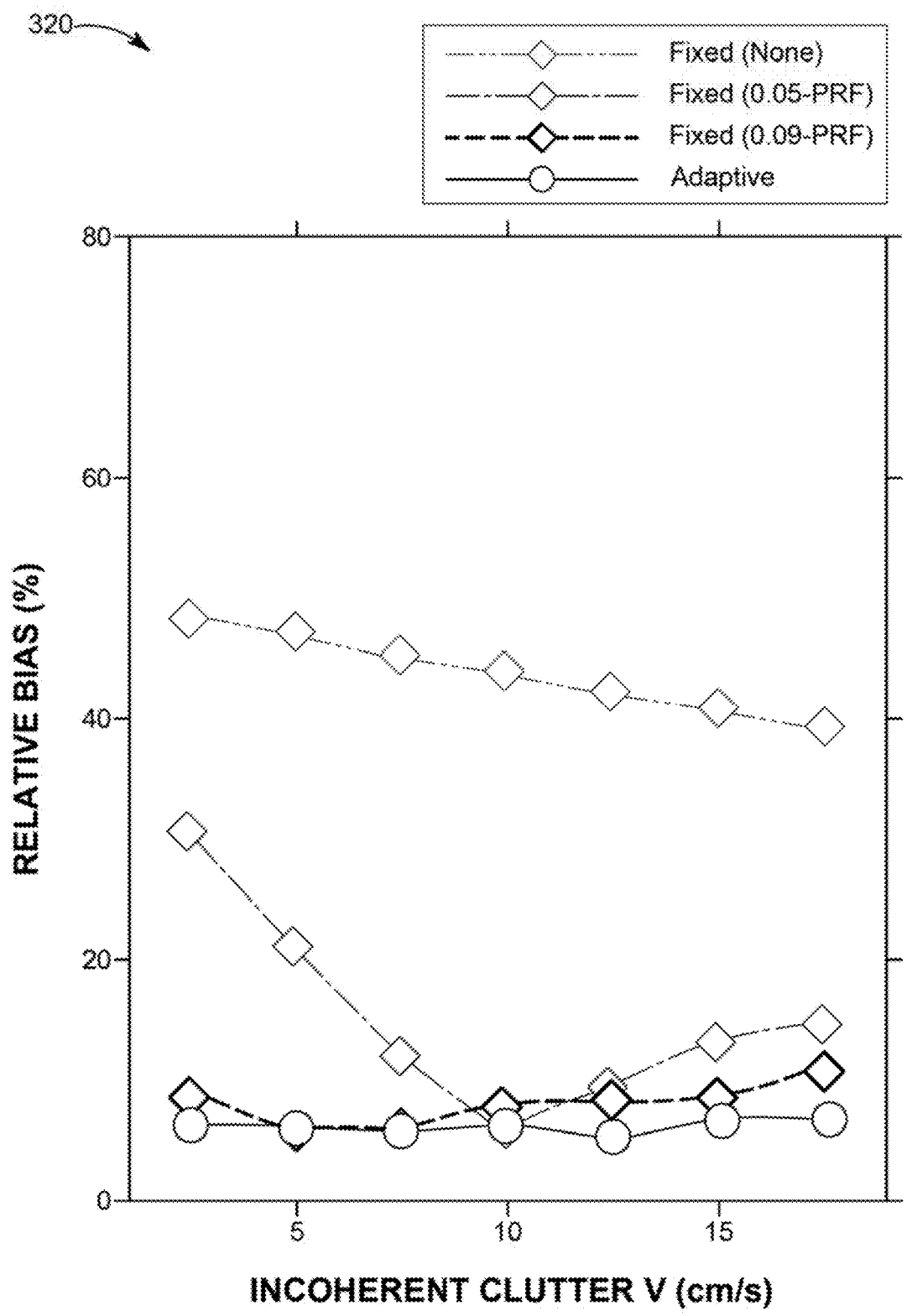
FIG. 3(B) shows a graph illustrating a comparison of the incoherent clutter of a coherence-adaptive filter versus a non-filter, a 0.05-PRF Filter, and a 0.09-PRF filter.
Figure 3C:
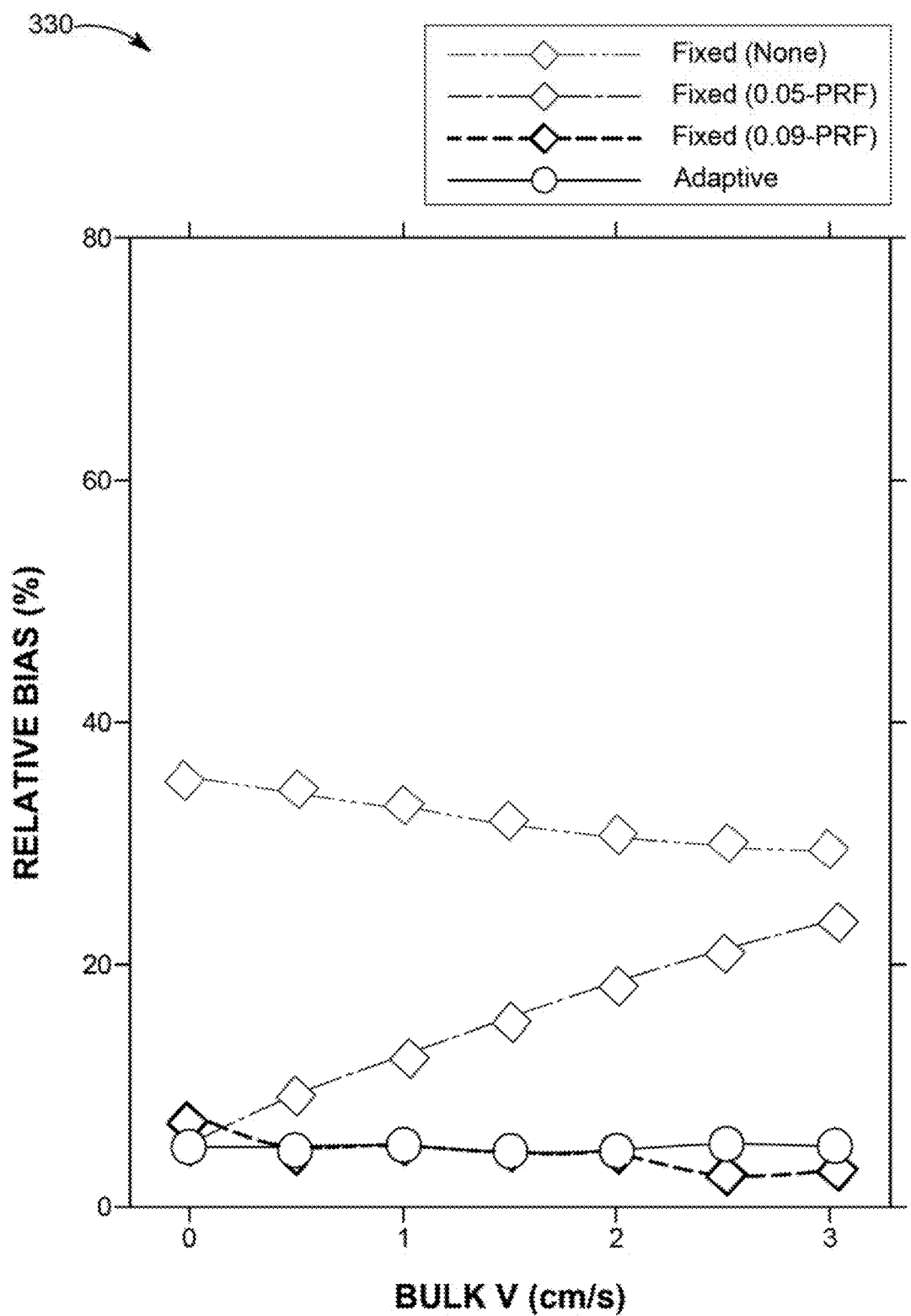
FIG. 3(C) depicts a graph illustrating a comparison of the bulk velocity of a coherence-adaptive filter versus a non-filter, a 0.05-PRF Filter, and a 0.09-PRF filter.

FIGS. 3(A)-(C) illustrates graphs that represent percent bias from true velocity measured in simulation. Peak flow velocity curves 310, incoherent clutter velocity curves 320, and bulk velocity curves 330 are shown. Each of the graphs 310, 320, and 330 compare a curve with no filtering, an 0.05 pulse repetition filter (PRF), a 0.09 PRF filter, and a coherence-adaptive filter.

In FIG. 3(A), the coherence adaptive filter shows minimal bias in comparison to the non-filter curve, the 0.05 PRF filter curve, and also the 0.09 PRF filter curve. The peak flow does not cause the coherence-adaptive filter to be unable to suppress bias from clutter. The coherence-adaptive clutter filtering is able to simultaneously suppress bias from clutter without compromising slow flow measurement.

In FIG. 3(B), the coherence-adaptive clutter filter also shows very little bias in comparison to the non-filter curve, and also the 0.05 PRF and 0.09 PRF filter curves. The coherence-adaptive filter is able to suppress bias when faced with varying levels of incoherent clutter.

Referring to FIG. 3(C), the coherence-adaptive clutter flitter suppresses bias due to clutter from nearby bright scatters moving with varying bulk velocities more than either the non-fixed filter curve or the 0.05 PRF filter curve. As with FIGS. 3(A) and 3(B), the coherence-adaptive clutter filter is able to able suppress bias under different simulated flow and noise conditions.

In FIGS. 3(A)-(C), with the measurements for varying peak flow velocity 310, incoherent clutter velocity 320, and bulk velocity 330 shown, the coherence adaptive filtering that is shown in the bottom of each graph 310, 320, and 330 reveals minimal bias under all simulated flow and noise conditions. Under either peak flow 310, incoherent clutter 320, or bulk velocity 330, the coherence-adaptive clutter filtering demonstrates the ability to simultaneously suppress bias from clutter as well or better than any of the other filters that are shown. In each situation, the spatial coherence-adaptive clutter filtering shows very minimal bias regardless of the conditions.

Figure 4A:
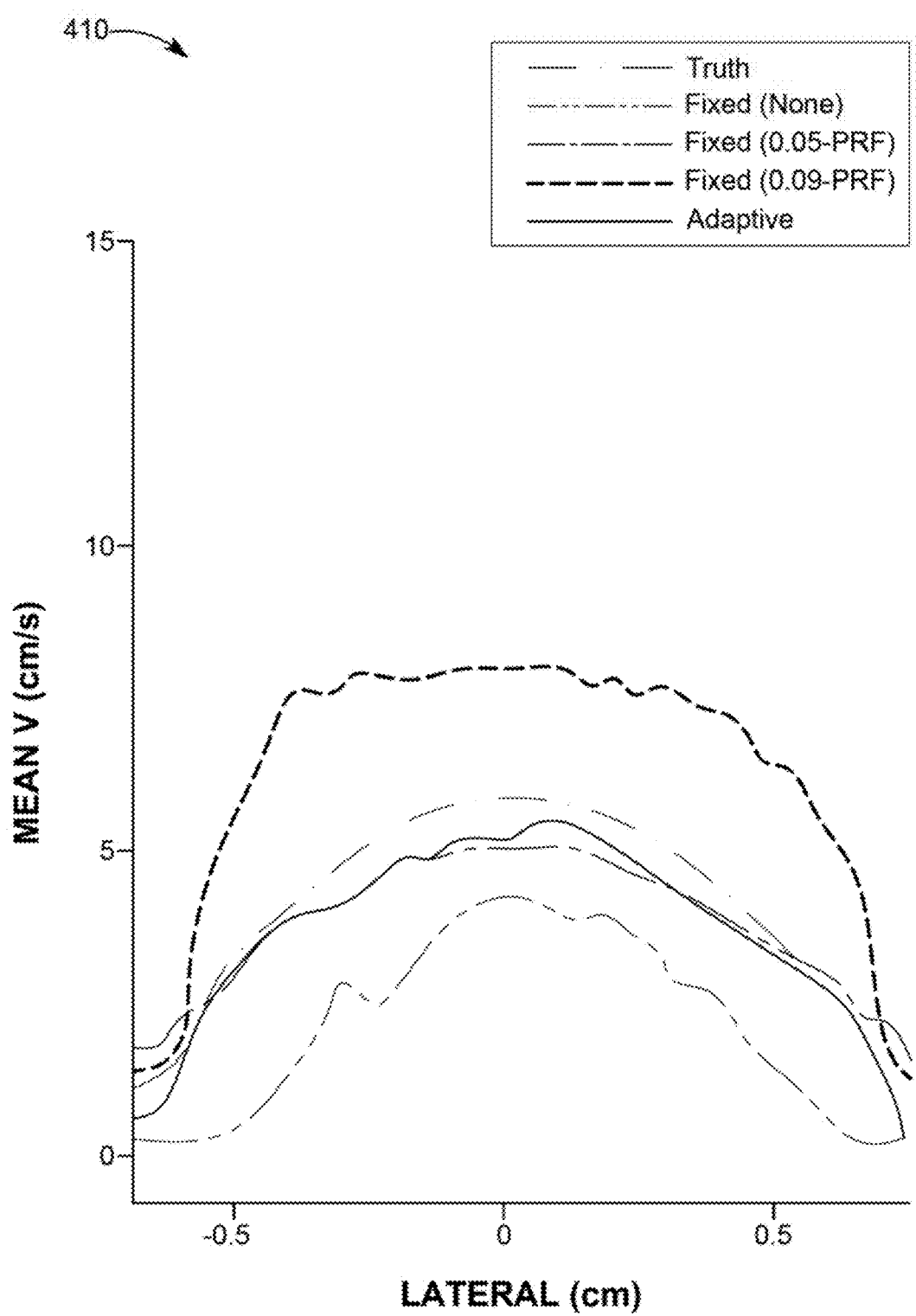
FIG. 4(A) depicts a graph illustrating a lateral velocity simulation of 6 cm/s slow flow with no filtering, a low fixed cutoff frequency filter, a high fixed cutoff frequency filter, and a coherence-adaptive clutter filter.
Figure 4B:
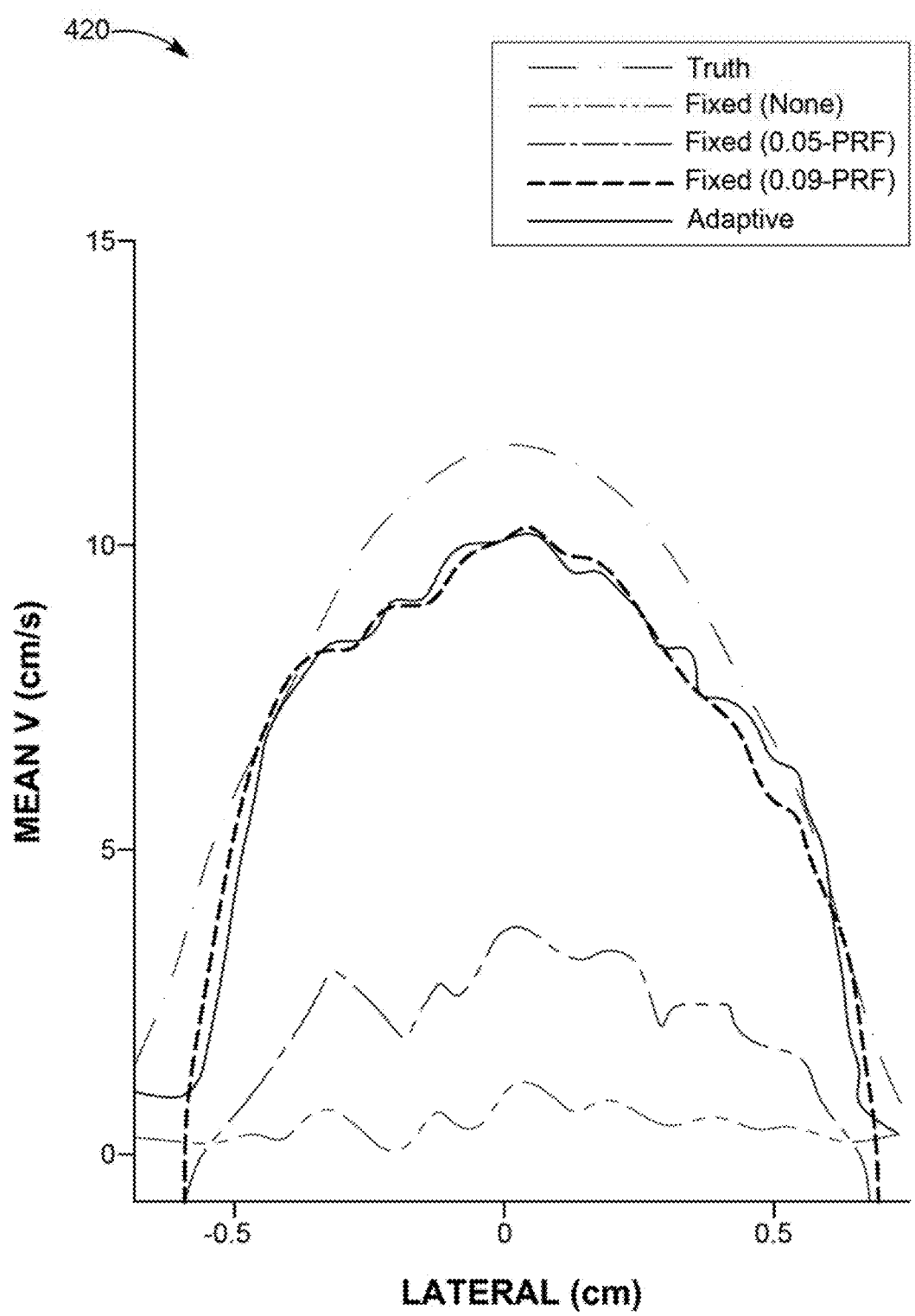
FIG. 4(B) depicts a graph illustrating a lateral velocity simulation of −1 cm/s moving incoherent clutter with no filtering, a low fixed cutoff frequency filter, a high fixed cutoff frequency filter, and a coherence-adaptive clutter filter.
Figure 4C:
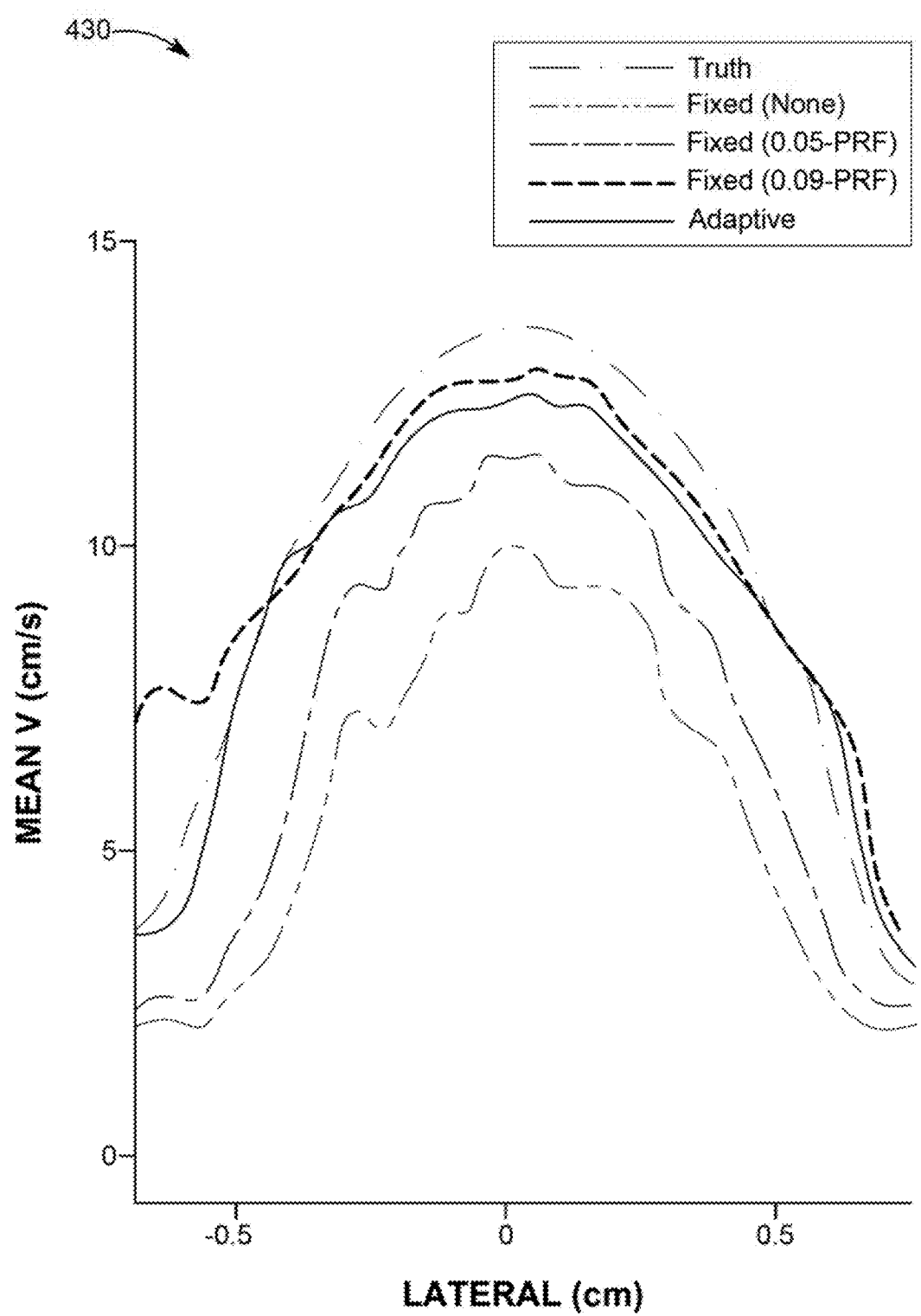
FIG. 4(C) shows a graph illustrating a lateral velocity simulation of 2 cm/s bulk motion with no filtering, a low fixed cutoff frequency filter, a high fixed cutoff frequency filter, and a coherence-adaptive clutter filter.

FIGS. 4(A)-(C) depict lateral velocity profile simulations 410, 420 and 430. Velocity profiles from a 6 cm/s simulation 410, −1 cm/s (incoherent clutter) simulation 420, and bulk motion simulation 430 are shown. In each graph 410, 420, 430, there is a curve with no filtering, IIR filtering with a fixed cutoff 0.05 PRF, a fixed cutoff 0.09 PRF, coherence-adaptive clutter filtering (adaptive clutter filtering), and also ground truth curve (actual flow profile).

In FIG. 4(A), In the 6 cm/s slow flow simulation 410, the coherence-adaptive clutter filtering curve is closest to the ground truth curve, or actual flow profile. More specifically, the coherence-adaptive clutter filtering curve is closer to the actual flow profile than the fixed 0.05 PRF curve, and also much closer to the actual flow profile than the non-filter curve and the fixed 0.09 PRF curve. In this simulation, the adaptive clutter filtering closely matches the best cutoff filter.

Referring to FIG. 4(B), in the −1 c/s moving incoherent clutter simulation 420, the coherence-adaptive clutter filtering curve is also much closer to the actual flow profile than the non-filter curve and the fixed 0.05 PRF curve, and also closer to the actual flow profile than the fixed 0.09 PRF curve. Moreover, the coherence-adaptive clutter filtering curve closely matches the 0.09 PRF curve that is closest to the actual flow profile.

In FIG. 4(C), in the 2 cm/s bulk motion simulation 430, the coherence-adaptive clutter filtering curve is closer to the actual flow profile/truth than the non-filter curve and the fixed 0.05 PRF curve. The coherence-adaptive clutter filtering curve also closely matches the fixed 0.09 PRF curve in relation to the actual flow profile. In each simulation 410, 420, and 430, the coherence-adaptive clutter filter curve is close to the actual flow profile and exhibits similar performance to the best-case fixed cutoff filter regardless of the conditions. In contrast, the other curves are not always closely matching the curve of the actual flow profile/truth.

FIGS. 5(A)-(E) illustrate a list of example phantom flow images. The contrast and resolution of the images are shown.

Figure 5A:
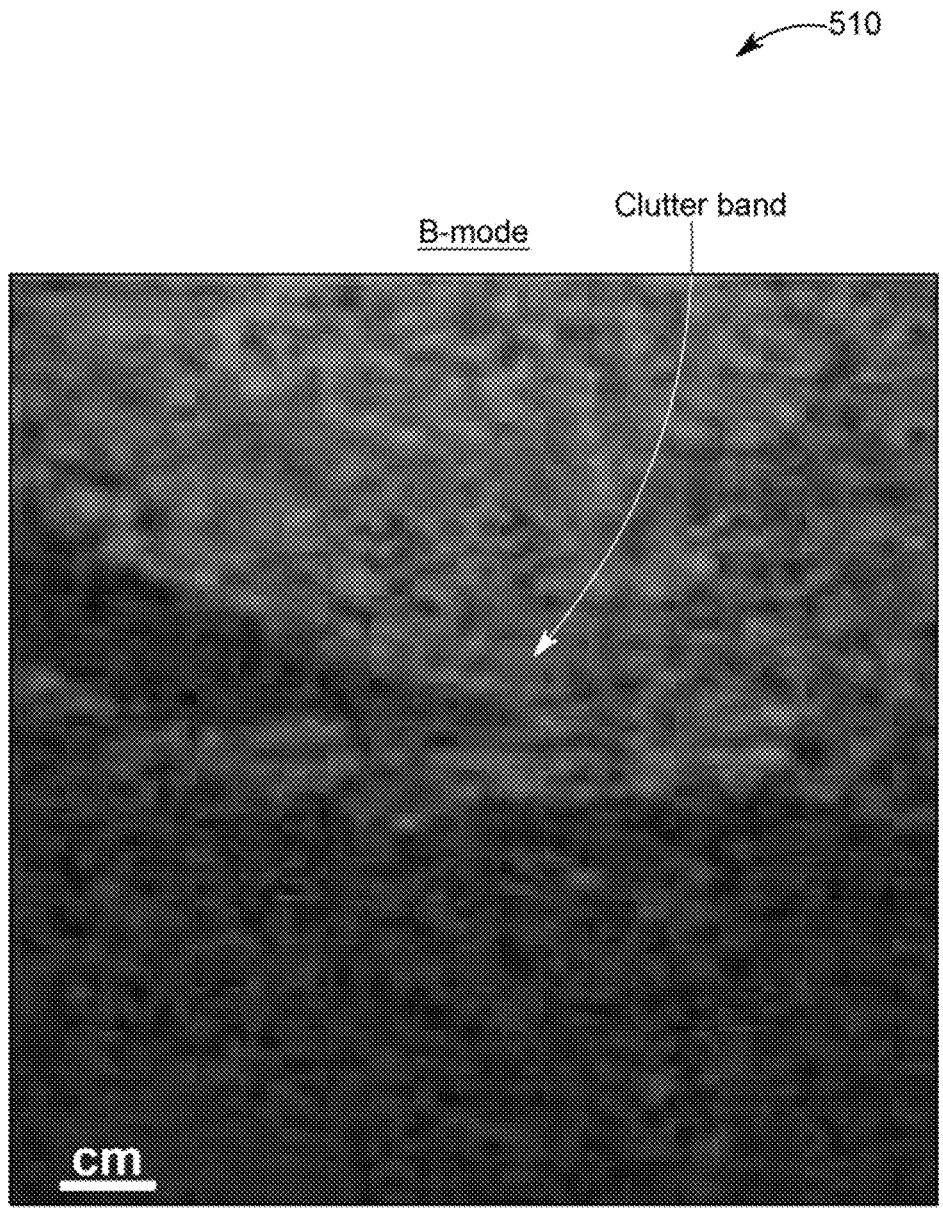
FIG. 5(A) depicts an example flow phantom image for a brightness (b) mode or a b-mode image.

In FIG. 5(A), a brightness mode (b-mode) image 510 is illustrated. The clutter band that is present in the b-mode image 510 gives the image less than ideal resolution and contrast for the b-mode image 510. The noticeable clutter band in the b-mode image 510 makes it harder to see a defined or clear image.

Figure 5B:
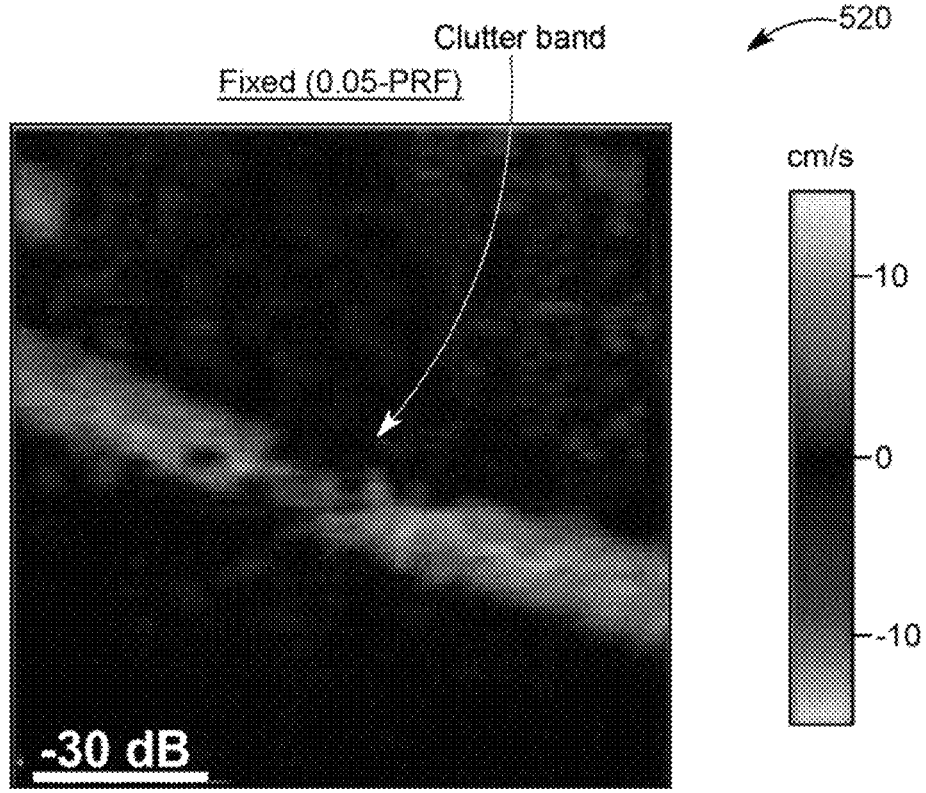
FIG. 5(B) shows an example flow phantom image for a low fixed cutoff clutter filtering image.

In FIG. 5(B), a fixed 0.05 PRF image 520 is illustrated. The fixed 0.05 PRF image 520 is also referred to as a CFI with low-fixed-cutoff-clutter filtering. The 0.05 PRF image has a clutter band. The low-fixed-frequency-cutoff filter is unable to minimize clutter, and the clutter band is still present within the fixed 0.05 PRF clutter band 520.

Figure 5C:
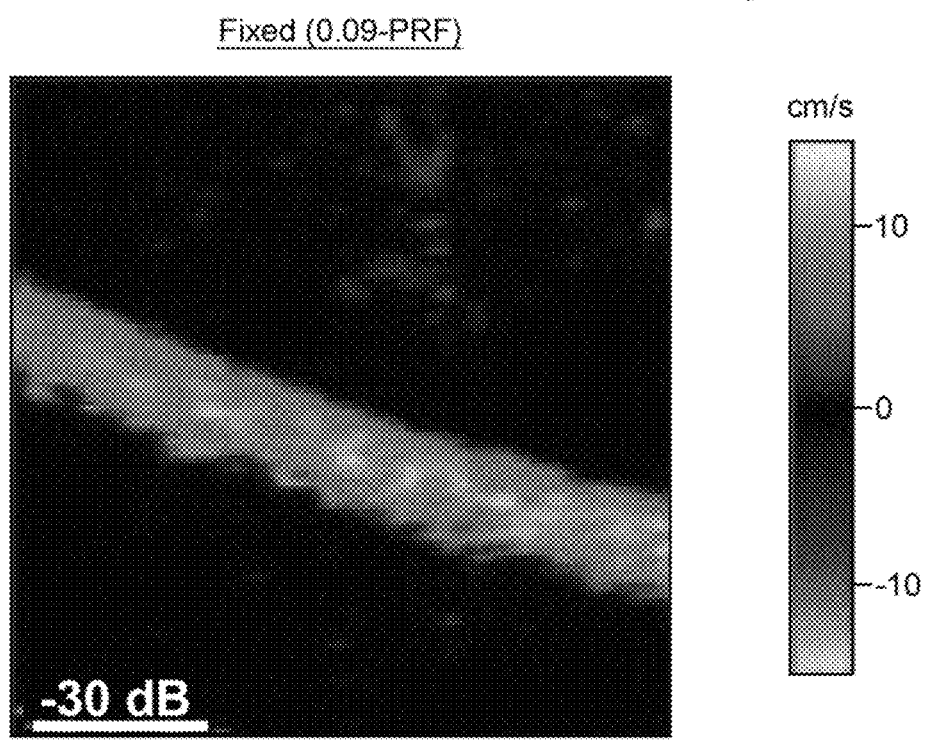
FIG. 5(C) depicts an example flow phantom image for a high fixed cutoff clutter filtering image.

Referring to FIG. 5(C), a fixed 0.09 PRF image 530 or a CFI with high fixed cutoff clutter filtering is illustrated. The fixed 0.09 PRF image 530 does not have a clutter band. In addition, the fixed 0.09 PRF image 540 has a better vessel definition and velocity estimation than the fixed 0.05 PRF image 520. The high-fixed-cutoff-clutter filtering prevents the clutter band that is present in the 0.05 PRF image 520 and thereby provides better vessel definition and velocity estimation.

Figure 5D:
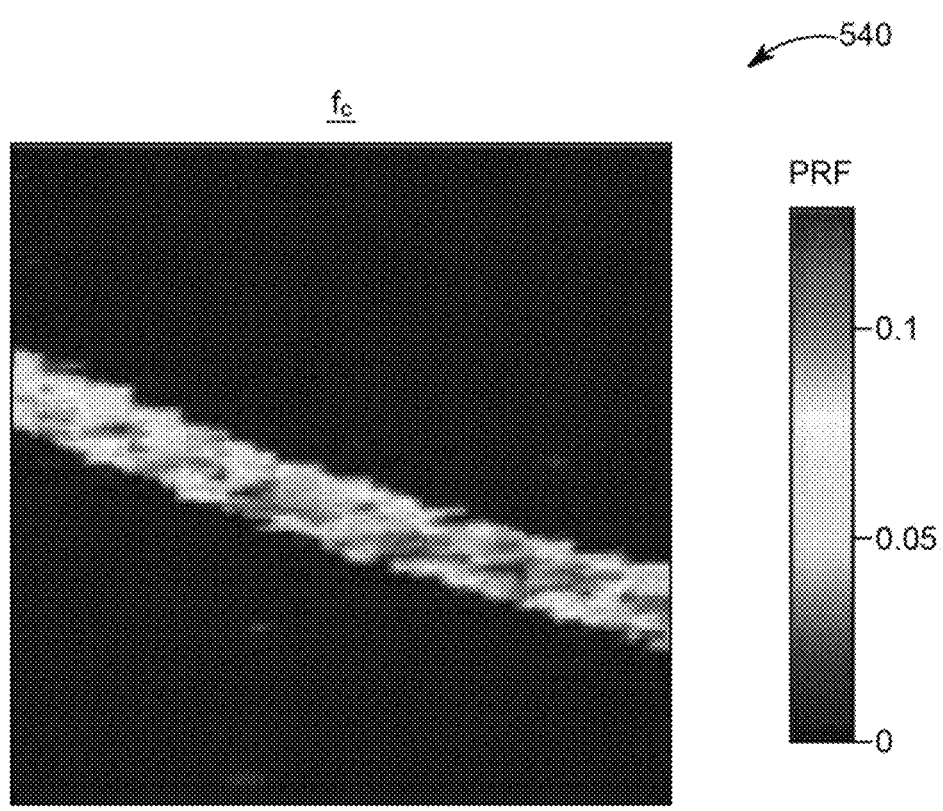
FIG. 5(D) illustrates an example flow phantom image for a coherence feedback image.

In FIG. 5(D), coherence feedback image 540 is shown. This image shows the cutoff frequencies of the filters that produce the best spatial coherence values. These filters are applied to ensemble echo data in each pixel in the image to generate the coherence-adaptive filtering image 550.

Figure 5E:
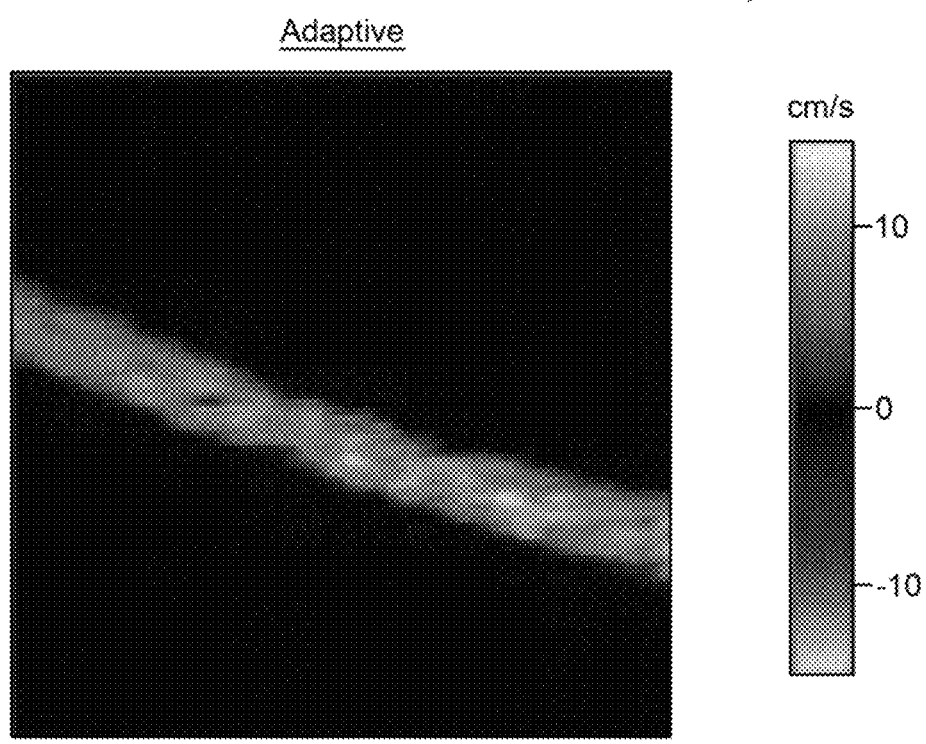
FIG. 5(E) shows an example flow phantom image for coherence-adaptive filtering image.

Referring to FIG. 5(E), a coherence-adaptive clutter filtering image 550 is illustrated. In comparison to the other images 510, 520, 530, and 540, the coherence-adaptive clutter filtering image 550 is free of the clutter band present in the B-mode image 510 and the 0.05 PRF image 520. Under cluttered conditions with approximately 7 cm/s flow, the selection of high cutoffs by the coherence-adaptive filtering image 550 substantially suppresses the clutter band present in the other images 510, 520. Moreover, fixed cutoff filter images are displayed with a −30 decibel (dB) power threshold in order to reduce any appearances of flash artifact or of thermal noise. The coherence-adaptive filtering enables for simultaneous measurement of velocity in both stationary and moving media. As a result, flash artifact and thermal noise free images can be obtained without power thresholding. Accordingly, the coherence-adaptive clutter filtering image 550 is obtained without power thresholding and free of flash artifact and thermal noise.

FIGS. 6(A)-(E) illustrate in vivo liver images. Moreover, B-mode, low fixed cutoff clutter filtering, high fixed cutoff clutter filtering, coherence feedback, and coherence-adaptive filtering images are shown as in FIGS. 5A-D, but with regard to in vivo liver images. One or more vessels are present in each of the images. Nevertheless, only the coherence-adaptive filtering image shows a plurality of vessels that are visualized simultaneously. The images include a B-mode image 610, a fixed 0.05 PRF image 620, a fixed 0.09 PRF image 630, filter cutoffs selected by coherence feedback, or a coherence feedback image 640, and a coherence-adaptive filtering image 650.

Figure 6A:
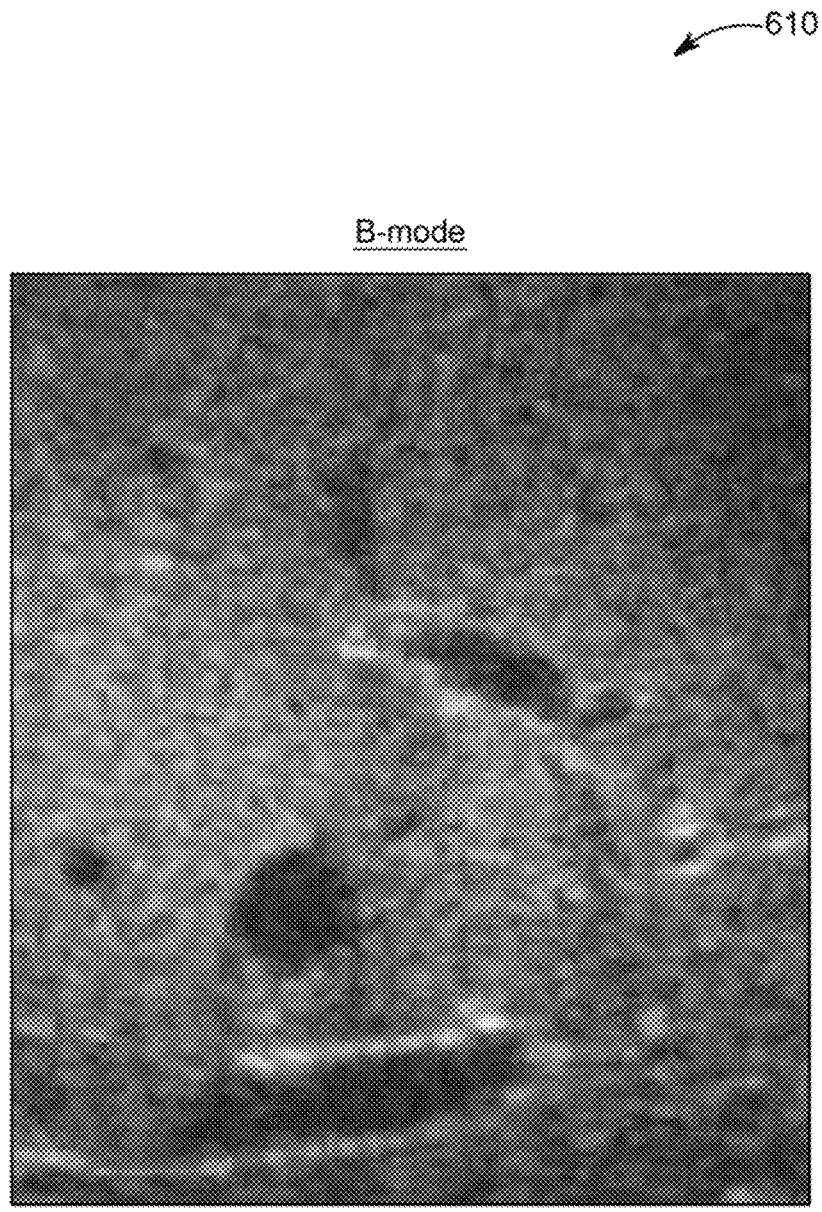
FIG. 6(A) depicts an in vivo liver images for a B-mode image.
Figure 6B:
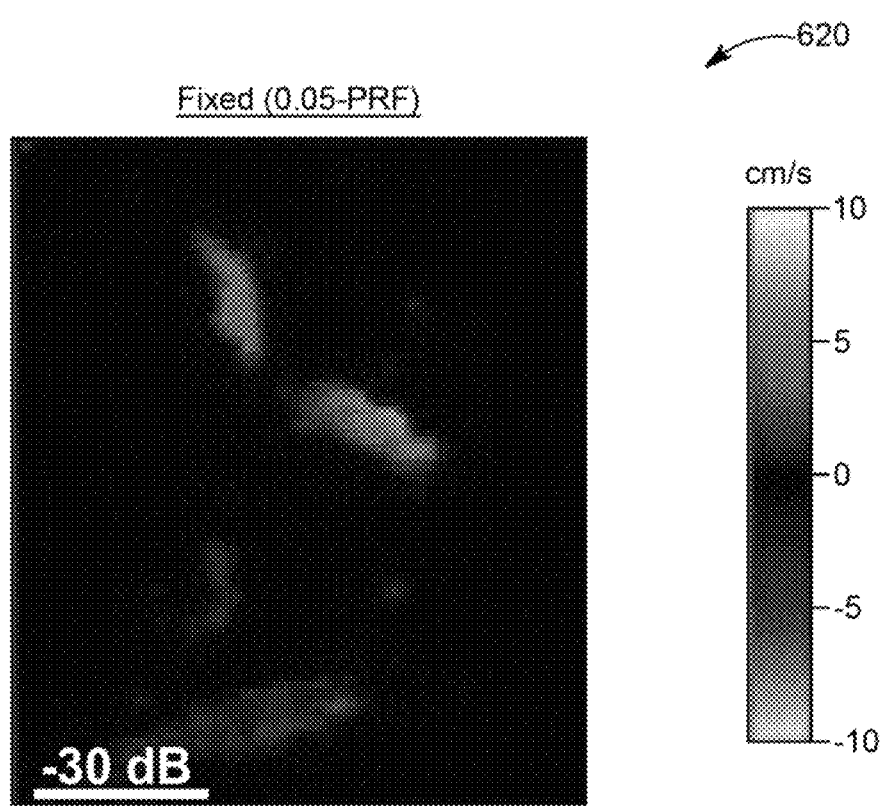
FIG. 6(B) shows an in vivo liver image for a low fixed cutoff clutter filtering image.

In FIG. 6(B), the fixed 0.05 PRF image 620 cannot effectively suppress clutter to be able to recover velocity information in certain vessels.

Figure 6C:
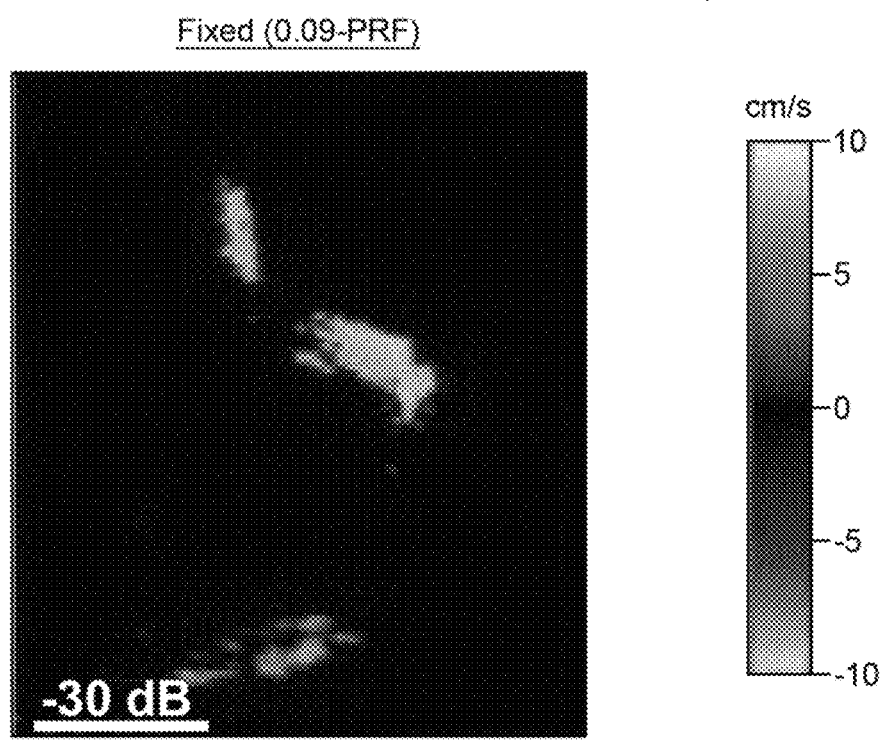
FIG. 6(C) illustrates an in vivo liver image for a high fixed cutoff clutter filtering image.

Referring to FIG. 6(C), the fixed 0.09 PRF image 630 is illustrated. The high-fixed-cutoff-clutter filtering or the fixed 0.09 PRF image 630 removes regions containing small vessels and slow-moving flow.

Figure 6D:
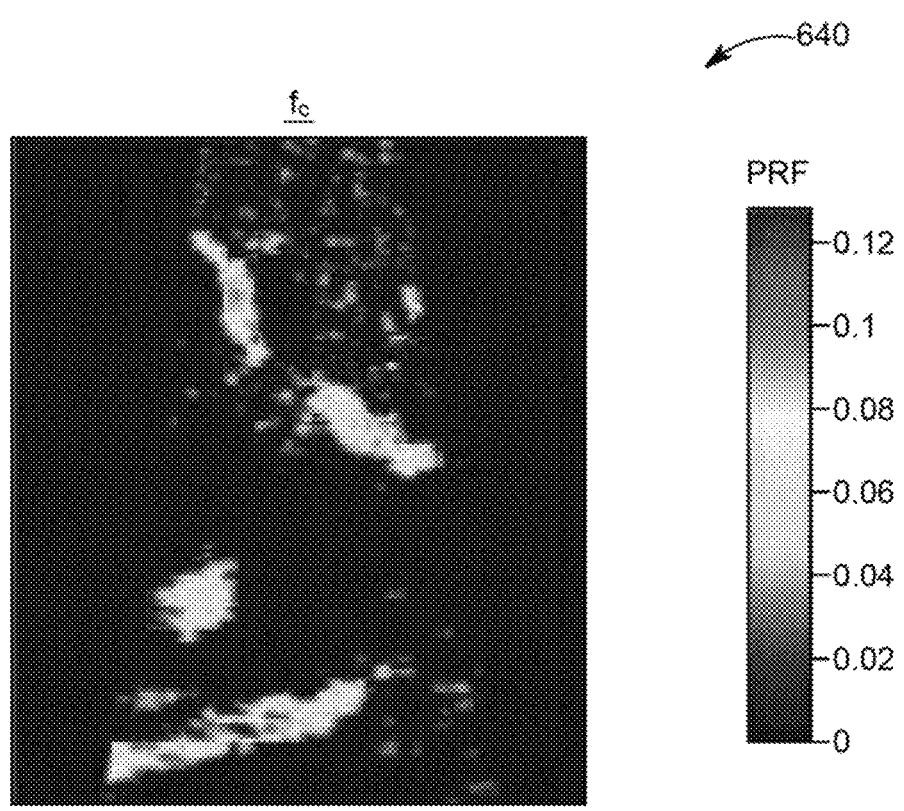
FIG. 6(D) depicts an in vivo liver image for a coherence feedback image.

In FIG. 6(D), the coherence feedback image 640 is shown. Spatial coherence feedback selects for a plurality of filters from the filter bank with different vessels revealing different optimal filter cutoff frequencies.

Figure 6E:
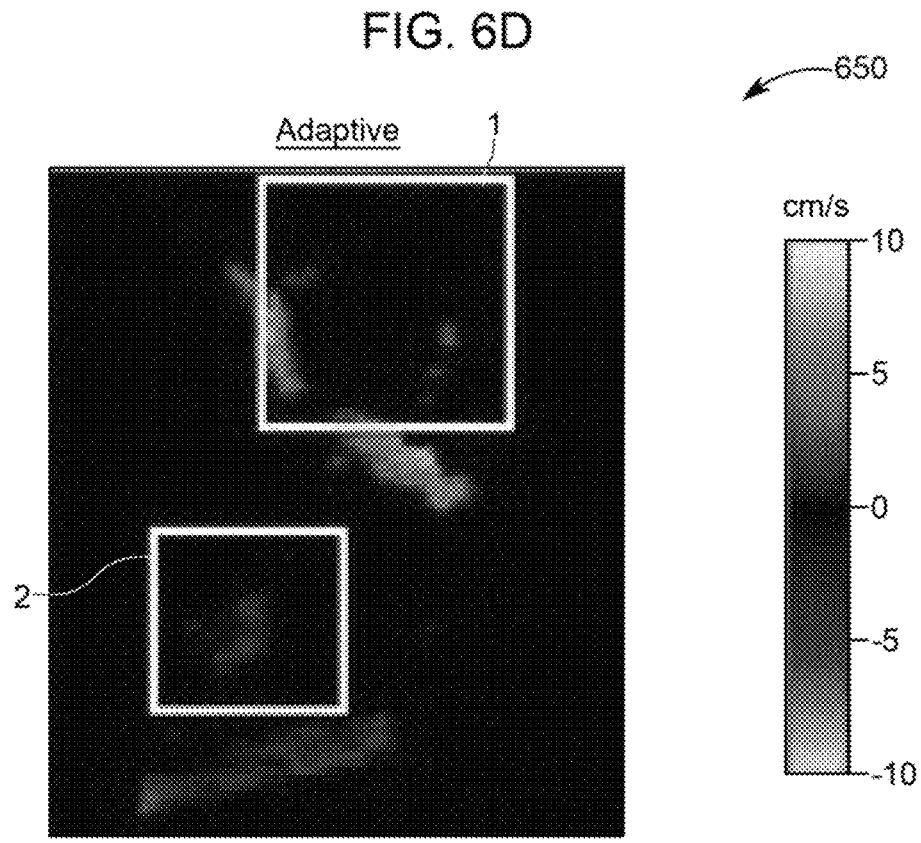
FIG. 6(E) shows an in vivo liver image for a coherence-adaptive filtering image.

Referring to FIG. 6(E), the coherence-adaptive filtering image 650 is distinguishable from the 0.05 PRF image 620 and the 0.09 PRF image 630. Moreover, the coherence-adaptive filtering image 650 is able to provide effective suppression of clutter in the image which the other images in the low-fixed-cutoff-clutter filtering, and the high-fixed-cutoff-clutter filtering are unable to achieve. Accordingly, the coherence-adaptive filtering image is able to show simultaneous visualization of small vessels (1) and the preservation of slow flow (2).

Figure 7:
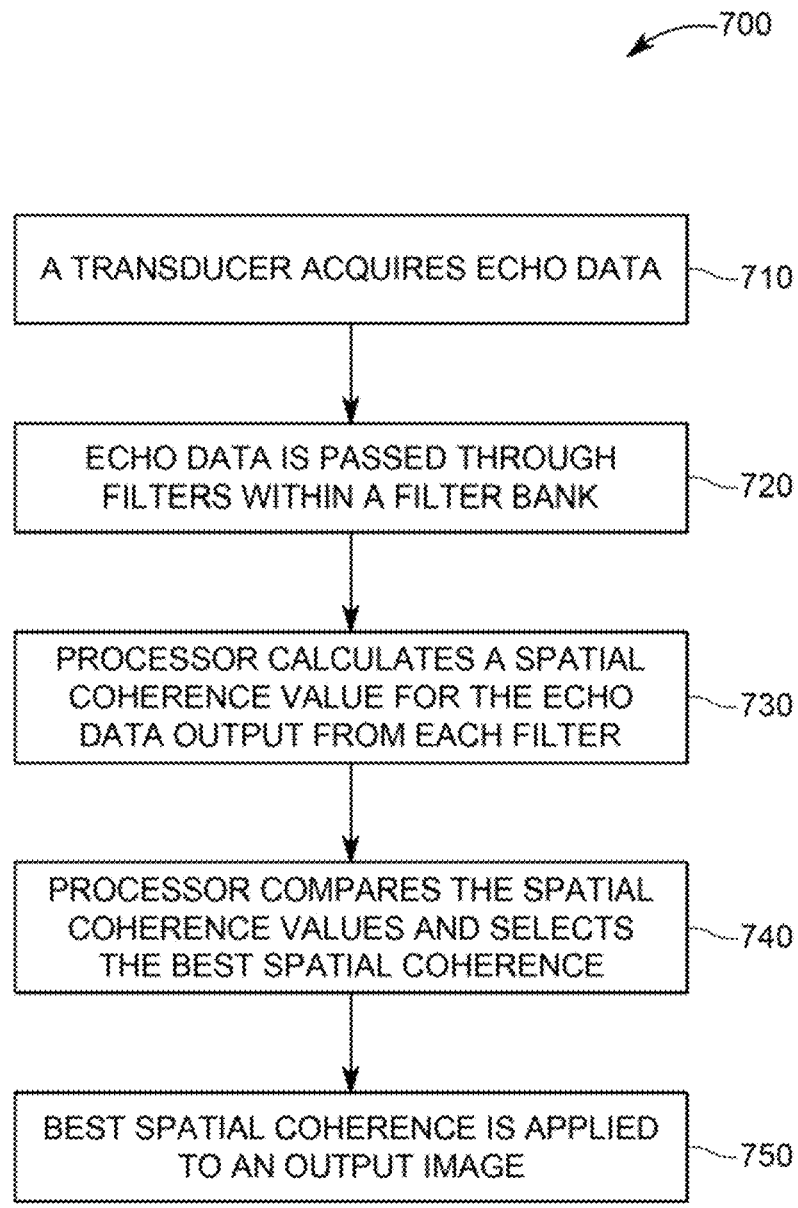
FIG. 7 depicts a flowchart depicting a process in accordance with an embodiment of the present invention.

FIG. 7 illustrates a process 700 for identifying a best spatial coherence value. Process 700 is a representative processing pipeline 200 suitable for use with ultrasound system 100. As noted above, ultrasound system 100 includes transducer 120, filter bank 220, and processor 130 to perform the processing steps that lead to identifying a best spatial coherence and a preferred filter to use for subsequent velocity estimations. Process 700 can be performed in real-time or post-acquisition to improve motion estimation accuracy on a per-pixel, per-region, or per-image basis.

At operation 710, transducer 120 acquires ensemble channel data/pulse-echo data. Transducer 120 acquires the pulse-echo data to enable ultrasound system 100 to ultimately identify the best spatial coherence. After acquiring the pulse-echo data, transducer 120 transmits the pulse-echo data to Filter bank 220 within control system 110. As such, the signal of the pulse-echo data passed through filter bank 220 to filter the pulse-echo data signal through a variety of frequency ranges.

At operation 720, Filter bank 220 is receive the pulse-echo data. Filter bank 220 filters each signal of the pulse-echo data through a different one of the plurality of filters Filter bank 220. In the depicted example, the clutter filters are IIR filters; however, in some embodiments, the clutter filters are a different type of filter, such as FIR, Eigen-filters, FFT filters, and the like. Each of the filters within filter bank 220 provides output echo data.

At operation 730, processor 130 calculates a spatial coherence value for the output echo data from each filter.

At operation 740, processor 130 creates a map of the spatial coherence values for the plurality of output signals from filter bank 220 and compares the spatial coherence values from each filter. Processor 130 also puts together a map of the velocity estimates as well. Further, processor 130 compares the spatial coherence values, and identifies the best spatial coherence value, and designates the filter that yielded the best spatial coherence value as the preferred filter for subsequent velocity estimations.

At operation 750, processor 130 uses the preferred filter for the subsequent velocity estimations for an output image for clinical use and applies the best spatial coherence value to the output image.

In summary, ultrasound system 100 filters a signal through a plurality of filters to obtain output echo data. Processor 130 calculates the spatial coherence values of the output pulse echo data, and creates a map of the spatial coherence values. From the map of the spatial coherence values, processor 130 identifies the best spatial coherence value and the corresponding filter, which is then designated as the preferred filter to be used for subsequent velocity estimations to generate an output image for clinical use. Processor 130 can also apply the best spatial coherence value to the output image. It should be noted that ultrasound system 100 can perform this process in real-time, or post-acquisition, based on target motion estimation accuracy.

It is to be understood that the disclosure teaches just some examples of embodiments in accordance with the present invention and that many variations of the invention can easily be devised by those skilled in the art after reading this disclosure and that the scope of the present invention is to be determined by the following claims.

What is claimed is:

1. An ultrasound system comprising:
   a transducer configured to acquire ensemble echo data;
   a filter bank comprising a first plurality of clutter filters, the filter bank being configured to receive the ensemble echo data from the transducer and generate, from each clutter filter, filtered echo data output; and
   a processor configured to (1) calculate a spatial coherence value from each filtered echo data output, (2) compare the spatial coherence values of the filtered echo data outputs to determine a best spatial coherence, (3) select, as a preferred filter for subsequent velocity estimations, the clutter filter associated with the best spatial coherence, and (4) generate an output image using the preferred filter.

2. The ultrasound system of claim 1 wherein the processor is further configured to generate a map of the plurality of spatial coherence values.

3. The ultrasound system of claim 1 wherein the filter bank comprises an Eigen-filter and an IIR filter, and the filter bank is configured to enable at least one filtered echo data output to pass through the Eigen-filter and IIR filter in real-time.

4. The ultrasound system of claim 1, wherein the processor is further configured to map the best spatial coherence to the output image.

5. The ultrasound system of claim 1 wherein the filter bank includes a second plurality of clutter filters, and wherein the processor is further configured to pass the ensemble echo data through the second plurality of clutter filters.

6. The ultrasound system of claim 1 wherein the preferred filter is selected in real-time based on a target motion estimation accuracy provided by measurements of spatial coherence.

7. The ultrasound system of claim 1 wherein the best spatial coherence is mapped to the output image in post-acquisition time based on a target motion estimation accuracy.

8. An ultrasound system comprising:
- a transducer configured to acquire and transmit ensemble echo data;
- a filter bank having a plurality of clutter filters configured to receive the ensemble echo data from the transducer, wherein the ensemble echo data is passed through the plurality of clutter filters, each of the clutter filters generating filtered ensemble echo data; and
- a processor configured to:
   - identify spatial coherence values from the filtered ensemble echo data from each clutter filter,
   - compare the spatial coherence values from the filtered ensemble echo data,
   - determine a best spatial coherence value from the identified spatial coherence values, wherein the best spatial coherence value is a highest among the set of spatial coherence values, and
   - identify the clutter filter having the best spatial coherence value for use for subsequent velocity estimations for generating an output image.

9. The ultrasound system of claim 8 wherein the processor is further configured to designate the clutter filter with the best spatial coherence value as a preferred filter.

10. The ultrasound system of claim 8 wherein the processor is further configured to (1) generate a map of the spatial coherence values from the filtered ensemble echo data and (2) determine the best spatial coherence value based on the map.

11. The ultrasound system of claim 8 wherein the processor is further configured to compare the spatial coherence values of each clutter filter in real-time based on a target motion estimation accuracy.

12. The ultrasound system of claim 8 wherein the filter bank further includes an FIR filter and an FFT filter, and wherein the ultrasound system is configured such that the echo data is passed through the FIR filter and the FFT filter in post-acquisition based on a target motion estimation accuracy.

13. The ultrasound system of claim 8 wherein the processor is further configured to generate a map of the spatial coherence values from the plurality of clutter filters in one of real-time and post-acquisition time based on a target motion estimation accuracy.

14. The ultrasound system of claim 8 wherein the processor is further configured to (1) use the filtered ensemble echo data from the plurality of clutter filters to generate a map of spatial coherence values and (2) identify the best velocity estimates based on the map of spatial coherence values.

15. A method for generating an output ultrasound image, the method comprising selecting a best spatial coherence by operations including:
- acquiring, by a transducer, ensemble echo data;
- receiving, by a filter bank comprising a plurality of clutter filters, the echo data from the transducer, wherein the echo data is passed through each clutter filter, each clutter filter generating filtered echo data output unique to the generating clutter filter;
- calculating, by a processor, a spatial coherence value for each filtered echo data;
- selecting a preferred filter from the plurality of clutter filters for subsequent velocity estimation, wherein the preferred filter is the clutter filter that yields the best spatial coherence, the best spatial coherence value is a highest among the plurality of spatial coherence values; and
- generating the output ultrasound image based on the best spatial coherence.

16. The method of claim 15 further comprising generating a map of velocity estimates and the spatial coherence based on the plurality of echo data outputs.

17. The method of claim 16 further comprising identifying the best spatial coherence based on the map of the spatial coherence values.

18. The method of claim 15 wherein the processor maps the best spatial coherence to the output image in real-time based on a target motion estimation accuracy.

19. The method of claim 15 further comprising generating a map of velocity estimates and the plurality of spatial coherence values in post-acquisition time based on a target motion estimation accuracy.

20. The method of claim 15 further comprising generating a map of the spatial coherence values to identify the best spatial coherence value based on a target motion estimation accuracy.

* * * * *